(12) United States Patent
Endo

(10) Patent No.: US 10,406,057 B2
(45) Date of Patent: Sep. 10, 2019

(54) STEP COUNTER, STEP ASSIST DEVICE, AND COMPUTER-READABLE MEDIUM HAVING STORED THEREON A STEP COUNT PROGRAM

(71) Applicant: HONDA MOTOR CO., LTD., Minato-Ku, Tokyo (JP)

(72) Inventor: Yosuke Endo, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 887 days.

(21) Appl. No.: 14/739,453

(22) Filed: Jun. 15, 2015

(65) Prior Publication Data

US 2015/0366740 A1 Dec. 24, 2015

(30) Foreign Application Priority Data

Jun. 19, 2014 (JP) .................................. 2014-126128

(51) Int. Cl.
*A61H 3/00* (2006.01)
*A61F 2/70* (2006.01)
(Continued)

(52) U.S. Cl.
CPC .................. *A61H 3/00* (2013.01); *A61F 2/70* (2013.01); *A61F 5/0102* (2013.01);
(Continued)

(58) Field of Classification Search
CPC .. A61H 3/00; A61H 1/0244; A61H 2201/164; A61H 2201/1628;
(Continued)

(56) References Cited

U.S. PATENT DOCUMENTS 8,298,164 B2 * 10/2012 Yasuhara ............. A61H 1/0244
482/66
9,682,006 B2 * 6/2017 Goldfarb ................. A61H 3/00
(Continued)

FOREIGN PATENT DOCUMENTS

| JP | 2011218026 A | 11/2011 |
|---|---|---|
| JP | 2012165790 A | 9/2012 |
| JP | 2014121491 A | 7/2014 |

OTHER PUBLICATIONS

Japanese Office Action of corresponding Japanese Patent Application No. 2014-126128 dated May 19, 2015 with English translation.
(Continued)

*Primary Examiner* — Sundhara M Ganesan

(57) ABSTRACT

When performing actuator control using weight on the bottom of the foot as a trigger, the foot of the user must appropriately touch the ground in order for the weight to be sensed. Therefore, the activation condition for starting the actuator control is limited and, for example, a rehabilitation patient who has one injured leg has difficulty training their step movement using this step assist device. Provided is a step assist device including a providing section that provides an assist force to a step movement of a user; a detecting section that detects a hip joint angle, which is an angle of aperture of a hip joint of the user; and a control section that begins controlling the providing section when the hip joint angle exceeds a predetermined threshold value, according to an assistance plan set in advance for the step movement of a single step of the user.

16 Claims, 12 Drawing Sheets

(51) Int. Cl.
*A61F 5/01* (2006.01)
*A61H 1/02* (2006.01)

(52) U.S. Cl.
CPC .... *A61H 1/0244* (2013.01); *A61F 2005/0155* (2013.01); *A61H 2003/007* (2013.01); *A61H 2201/1215* (2013.01); *A61H 2201/164* (2013.01); *A61H 2201/165* (2013.01); *A61H 2201/1628* (2013.01); *A61H 2201/5069* (2013.01)

(58) Field of Classification Search
CPC ...... A61H 2201/1215; A61H 2201/165; A61H 2003/007; A61H 2201/5069; A61F 5/0102; A61F 2/70; A61F 2005/0155
See application file for complete search history.

(56) References Cited

U.S. PATENT DOCUMENTS 9,849,004 B2 * 12/2017 Choi .................. A61F 2/68
2010/0049102 A1 * 2/2010 Yasuhara ............. A61H 1/0244
                                                            601/5
2011/0288453 A1    11/2011 Endo
2012/0165817 A1 *  6/2012 Selig .................... A61B 5/6885
                                                            606/48
2012/0310122 A1   12/2012 Endo et al.
2013/0165817 A1 *  6/2013 Horst ................... A61F 5/0102
                                                            600/587
2014/0121575 A1    5/2014 Yasuhara et al.
2015/0142130 A1 *  5/2015 Goldfarb ............... A61H 1/024
                                                            623/25

OTHER PUBLICATIONS

Japanese Office Action of corresponding Japanese Patent Application No. 2014-126128 dated Sep. 15, 2015 with English translation.
German Examination Report dated May 3, 2016 with English translation for corresponding German File No. 10 2015 211 267.5.

* cited by examiner

STEP COUNTER, STEP ASSIST DEVICE, AND COMPUTER-READABLE MEDIUM HAVING STORED THEREON A STEP COUNT PROGRAM

BACKGROUND

The content of the following Japanese application is incorporated herein by reference:
NO. 2014-126128 filed on Jun. 19, 2014.

TECHNICAL FIELD

The present invention relates to a step assist device and a step assist program.

RELATED ART

A step assist device is known that begins actuator control for one step, in response to the weight placed on the bottom of a foot exceeding a predetermined first threshold value and then dropping below a second predetermined threshold value, as shown in Patent Document 1, for example.

Patent Document 1: Japanese Patent Application Publication No. 2011-218026

When performing actuator control using weight added on the bottom of the foot as a trigger, it is necessary for the foot of the user to appropriately touch the ground in order for the weight to be sensed. Therefore, the activation condition for starting the actuator control is limited and, for example, it is difficult for a rehabilitation patient who has one injured leg to train their step movement by using this step assist device.

SUMMARY

According to a first aspect of the present invention, provided is a step assist device comprising a providing section that provides an assist force to a step movement of a user; a detecting section that detects a hip joint angle, which is an angle of aperture of a hip joint of the user; and a control section that begins controlling the providing section when the hip joint angle exceeds a predetermined threshold value, according to an assistance plan that is set in advance for the step movement of a single step of the user.

According to a second aspect of the present invention, provided is a computer-readable medium storing thereon a step assistance program that, when executed by a computer, causes the computer to detect a hip joint angle, which is an angle of aperture of a hip joint of a user; and begin controlling a providing section that provides an assist force for a step movement when the hip joint angle exceeds a predetermined threshold value, according to an assistance plan that is set in advance for the step movement of a single step of the user.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
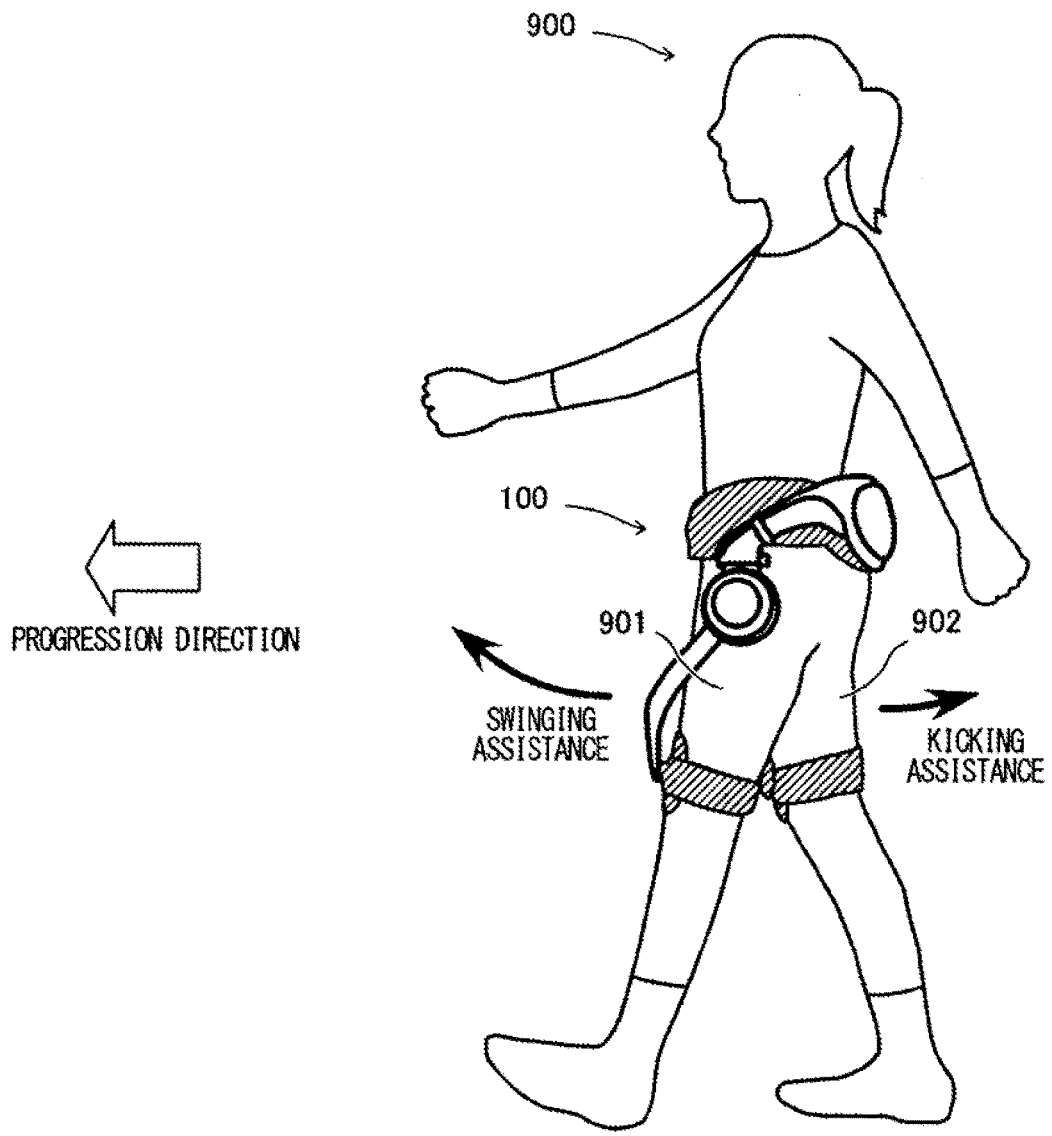
FIG. 1 is a view for describing a usage state of a step assist device according to the present embodiment.

FIG. 1 is a view for describing a usage state of a step assist device 100 according to the present embodiment. A user 900 attaches and secures the step assist device 100 to the waist and leg regions. The step movement of a person generally includes alternating repetition of a movement of kicking out the pivot leg and a movement of swinging forward the other leg. For example, as shown in the drawing, when the right leg is the pivot leg and the left leg is swung, the step assist device 100 assists with the kicking by applying a backward assist force to the right thigh 902 and assists with the swinging by applying a forward assist force to the left thigh 901. On the other hand, when the left leg is the pivot leg and the right leg is swung, the step assist device 100 assists with the kicking by applying a backward assist force to the left thigh 901 and assists with the swinging by applying a forward assist force to the right thigh 902. By repeating the assistance movement, the step assist device 100 can provide an assist force for forward progression, thereby enabling the user 900 to walk comfortably.

The step assist device 100 is not limited to use by an able-bodied person. The step assist device 100 is also used by patients in rehabilitation who are training to recover their normal walking ability. For example, a rehabilitation patient who has suffered partial paralysis as the result of a stroke is prone to stumble when walking, due to a decrease in the knee joint angle during the swing phase, which is the interval during which the leg swings, and this is known to cause gait problems such as pulling up on the pelvis. The step assist device 100 can increase the knee joint angle by providing swing assistance, and is therefore suitable for use in rehabilitation after a stroke. Accordingly, the step assist device 100 can rectify the gait at an early stage and in a manner appropriate for the state of the rehabilitation patient. Furthermore, as another aspect, the step assist device 100 can decrease the physical exertion of a physical therapist who would have, up to this point, been giving rehabilitation treatment by moving while supporting the legs of the rehabilitation patient.

In addition, the step assist device 100 is not limited to being used by people, and can be applied to animals and machines. The step assist device 100 is not limited to providing assistance, and can also operate to provide resistance. In other words, the step assist device 100 can generate a resistance force that applies a backward assist force against the swinging movement and a forward assist force against the kicking movement of the user 900. By operating in this manner, the step assist device 100 can be used as a training device to for strength training by an athlete, for example.

The present embodiment describes a case in which the assist force is applied for assistance. In particular, the present embodiment describes a case in which the assist force is used for step training, which is training that is repeated for every step. In step training, the assist force is provided mainly to correct the gait of the user 900, and making the steps of the user 900 easier is a secondary concern. The following provides a detailed description of the step assist device 100.

Figure 2:
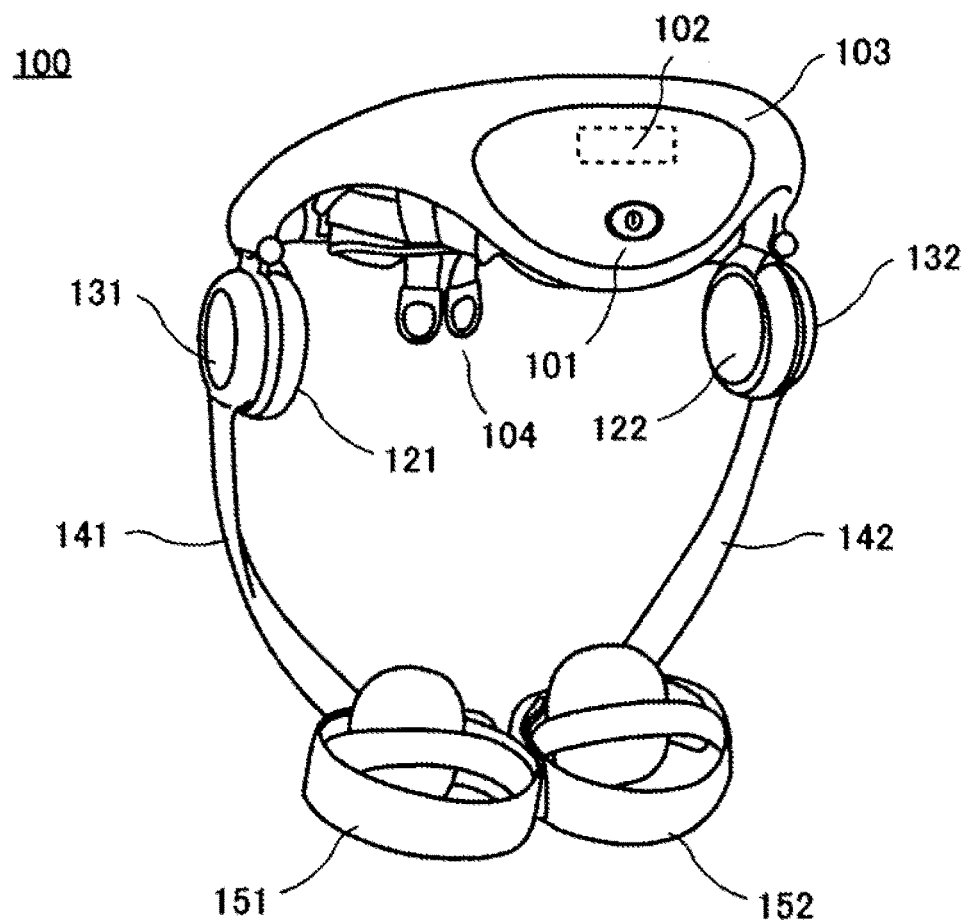
FIG. 2 is an external perspective view of the step assist device.

FIG. 2 is an external perspective view of the step assist device 100. The step assist device 100 includes a waist frame 103 that presses against the sides of the waist region from the back of the waist region of the user 900. The waist frame 103 is formed from a highly rigid material such as a light-weight alloy, e.g. aluminum, resin, e.g. polycarbonate, or carbon fiber. An activation switch 101 is provided near the center of the back surface of the waist frame 103, and the step assist device 100 can be made to operate when the user 900 presses the switch. Furthermore, the step assist device 100 can be made to stop when the switch is pressed once again.

A battery 102, which supplies electrical power to the step assist device 100, is arranged in an attachable manner on the back surface of the waist frame 103. The battery 102 may be a lithium ion battery with an output voltage of approximately 20 V, for example.

A waist belt 104 is connected to the ends of the waist frame 103. The waist belt 104 is wound around the waist of the user 900 together with the waist frame 103, and is fastened on the stomach surface side. The waist belt 104 is formed by a soft material such as a textile material. In this way, by using the waist frame 103 and the waist belt 104, the step assist device 100 is securely fastened to the user 900.

A left motor 121 and a right motor 122, which are each an example of an actuator, are arranged on both of the waist side surfaces of the waist frame 103. The left motor 121 and the right motor 122 are motors with the same specifications, and are DC motors having an output capability with a maximum torque of 4 N·m, for example. The left motor 121 rotates a left thigh frame 141 relative to the waist frame 103. The left thigh frame 141 is provided with a left angle sensor 131 that detects the rotational angle and rotational speed of the output rotation axis of the left motor 121. In the same manner, the right motor 122 rotates a right thigh frame 142 relative to the waist frame 103. The right thigh frame 142 is provided with a right angle sensor 132 that detects the rotational angle and rotational speed of the output rotation axis of the right motor 122. The left angle sensor 131 and the right angle sensor 132 are rotary encoders, for example.

The left thigh frame 141 and the right thigh frame 142 are formed from a highly rigid material such as a light-weight alloy, e.g. aluminum, resin, e.g. polycarbonate, or carbon fiber, in the same manner as the waist frame 103. A left thigh belt 151 is attached to the left thigh frame 141 on another end thereof that is opposite the one end to which the left motor 121 is connected. The user 900 winds and secures the left thigh belt 151 around the thigh of the left leg near the knee. In the same manner, a right thigh belt 152 is attached to the right thigh frame 142 on another end thereof that is opposite the one end to which the right motor 122 is connected. The user 900 winds and secures the right thigh belt 152 around the thigh of the right leg near the knee. The left thigh belt 151 and the right thigh belt 152 are formed of a soft material, such as a textile material.

With the step assist device 100 configured in this manner, when the left motor 121 is not being powered, the left angle sensor 131 can detect the rotational angle of the left thigh 901 during the step movement of the user 900 by their own strength. When the left motor 121 is powered and rotates forward, the left motor 121 rotates the left thigh frame 141 in the swinging direction, and as a result generates an assist force that lifts the thigh of the left leg forward. When the left motor 121 is powered and rotates backward, the left motor 121 rotates the left thigh frame 141 in the kicking direction, and as a result generates an assist force that presses the thigh of the left leg downward. In this way, the left motor 121 functions as a providing section that provides assist force to the step movement of the user 900. The left angle sensor 131 also detects the rotational angle of the left thigh 901 when the left motor 121 is being powered.

In the same manner, when the right motor 122 is not being powered, the right angle sensor 132 can detect the rotational angle of the right thigh 902 during the step movement of the user 900 by their own strength. When the right motor 122 is powered and rotates backward, the right motor 122 rotates the right thigh frame 142 in the swinging direction, and as a result generates an assist force that lifts the thigh of the right leg forward. When the right motor 122 is powered and rotates forward, the right motor 122 rotates the right thigh frame 142 in the kicking direction, and as a result generates an assist force that presses the thigh of the right leg downward. In this way, the right motor 122 functions as a providing section that provides assist force to the step movement of the user 900. The right angle sensor 132 also detects the rotational angle of the right thigh 902 when the right motor 122 is being powered.

In the manner described above, the step assist device 100 can provide assist force for assisting at least one of extension movement of the right leg, flexion movement of the right leg, extension movement of the left leg, and flexion movement of the left leg. Details of the extension movement and the flexion movement are described below using FIG. 3. Although a more detailed explanation is provided further below, in the present embodiment, in an example of performing rehabilitation on the right leg, the step assist device 100 provides an assist force that assists with the flexion movement of the right leg and an assist force that assists with the extension movement of the left leg.

Figure 3:
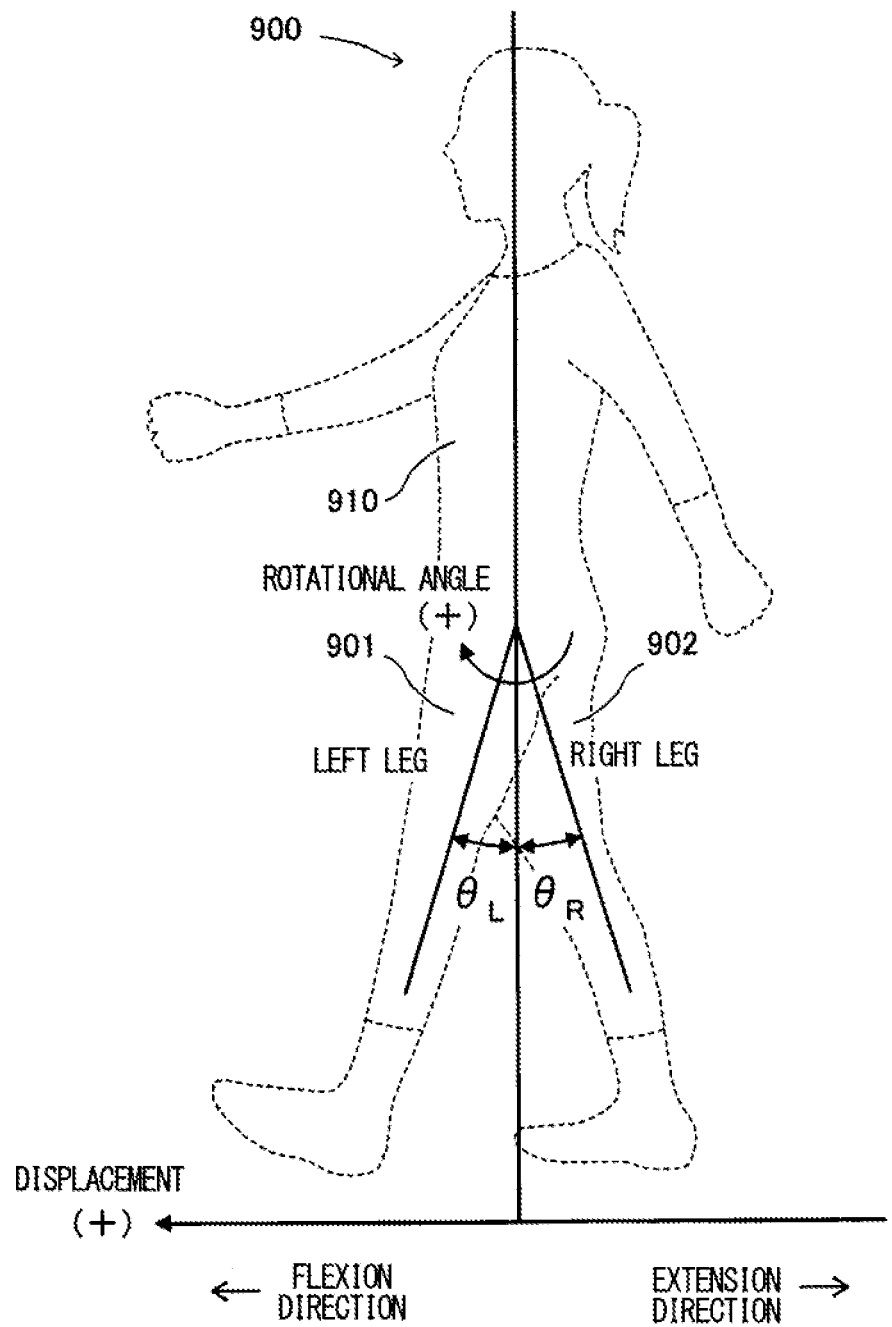
FIG. 3 is a view for describing the definition of the rotational angle and the movement of the user.

FIG. 3 is a view for describing the definition of the rotational angle and the movement of the user 900. As shown in the drawing, the direction of the displacement occurring when the user 900 progresses forward is set as the positive direction. During the swinging movement, the thighs are relatively close the upper body 910, and this is referred to as flexion movement. During flexion movement, the displacement direction is the positive direction. Furthermore, with a center line along the weight direction of the upper body 910 serving as a base line, the line portion along a thigh and having a hip joint as one end forms a positive rotation angle relative to the base line. In the drawing, the left leg is in the midst of the swinging movement, and the left hip join angle $\theta_L$, which is the angle formed by the line portion along the left thigh 901 relative to the base line, has a positive value.

During the kicking movement, the thighs are relatively far from the upper body 910, and this is referred to as extension movement. During extension movement, the displacement direction is the negative direction. Furthermore, the line portion along the thigh with the hip joint as one end forms a negative rotational angle relative to the base line. In the drawing, the right leg is in the midst of the kicking movement, and the right hip join angle $\theta_R$, which is the angle formed by the line portion along the right thigh 902 relative to the base line, has a negative value.

Figure 4:
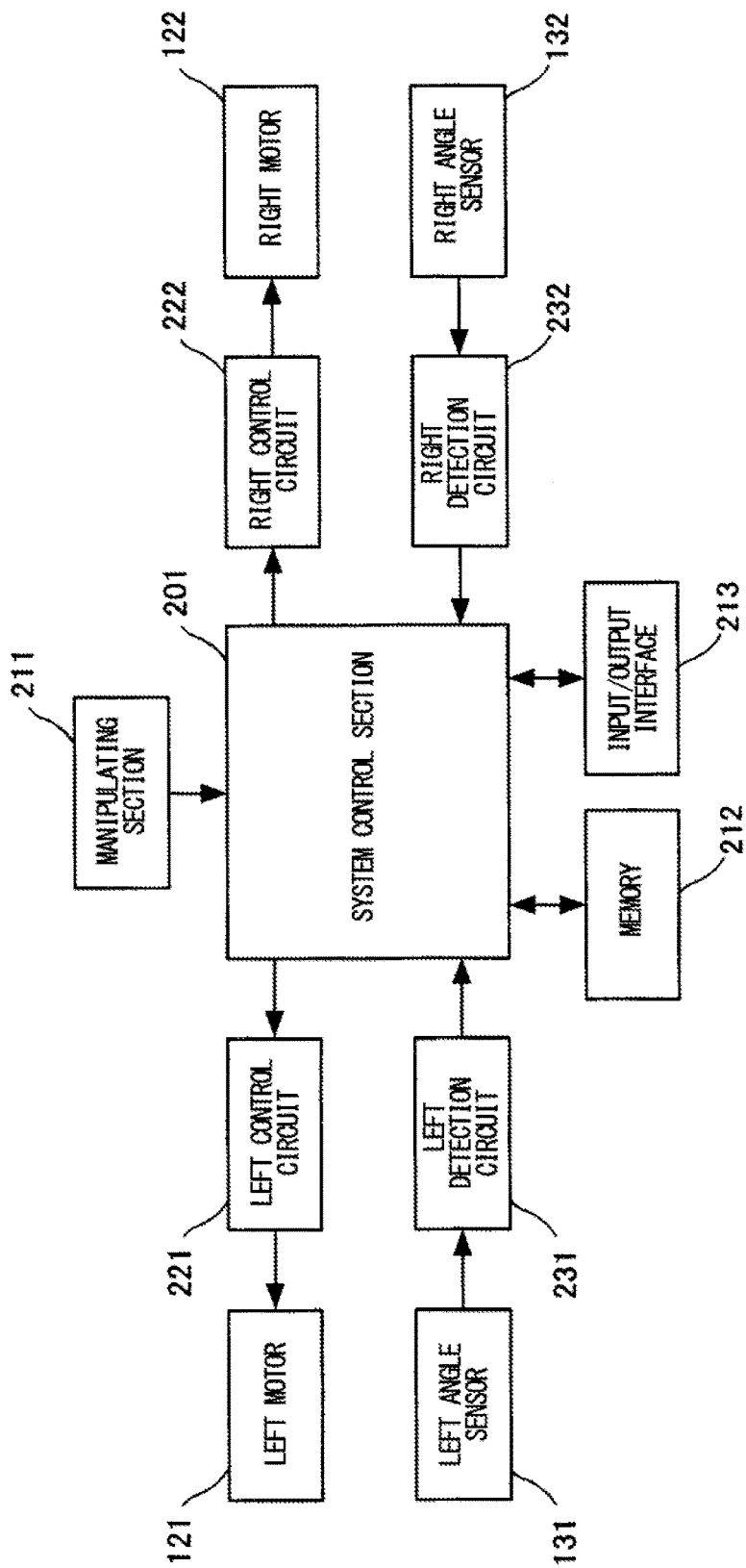
FIG. 4 is an element block diagram for describing each control element forming the step assist device.

The following describes each control element forming the step assist device 100. FIG. 4 is an element block diagram for describing each control element forming the step assist device 100. As shown in the drawing, each control element forming the step assist device 100 performs at least one of input and output either directly or indirectly with the system control section 201. In other words, the system control section 201 acting as a CPU that executes a preset program performs overall control of these control elements.

The system control section 201 controls the left motor 121 via a left control circuit 221. In the same manner, the system control section 201 controls the right motor 122 via a right control circuit 222. Specifically, after the assist force for assisting the left leg is calculated, the system control section 201 provides the left control circuit 221 with calculation results at a timing for generating this assisting assist force, and after the assist force for assisting the right leg is calculated, the system control section 201 provides the right control circuit 222 with calculation results at a timing for generating this assisting assist force. The left control circuit 221 and the right control circuit 222 each generate an analog drive voltage according to the provided calculation results, and respectively apply this drive voltage to the left motor 121 and the right motor 122. In other words, the left control circuit 221 and the right control circuit 222 have amplification circuits including DA converters.

The system control section 201 receives a detection result of the left angle sensor 131 via a left detection circuit 231. In the same manner, the system control section 201 receives a detection result of the right angle sensor 132 via a right detection circuit 232. Specifically, the left angle sensor 131 is made to continuously generate a voltage pulse according to the rotational angle of the left thigh 901. The left detection circuit 231 counts this voltage pulse to convert the voltage pulse into a rotation angle per unit time, and provides, per unit time, the system control section 201 with this rotational angle as a digital value. The system control section 201 can continuously be aware of the left hip angle $\theta_L$ shown in FIG. 3 by calculating the rotational angle from an activation time for each unit time. The left detection circuit 231 can also detect the rotational speed, by counting the voltage pulses in a prescribed time. The left detection circuit 231 supplies the rotational speed to the system control section 201. In the manner described above, the left angle sensor 131 and the left detection circuit 231 function as a detecting section that detects the left hip joint angle and the left hip joint angular speed of the user 900.

In the same manner, the right angle sensor 132 is made to continuously generate a voltage pulse according to the rotational angle of the right thigh 902. The right detection circuit 232 counts this voltage pulse to convert the voltage pulse into a rotation angle per unit time, and provides, per unit time, the system control section 201 with this rotational angle as a digital value. The system control section 201 can continuously be aware of the right hip angle $\theta_R$ shown in FIG. 3 by calculating the rotational angle from an activation time for each unit time. The right detection circuit 232 can also detect the rotational speed, by counting the voltage pulses in a prescribed time. The right detection circuit 232 supplies the rotational speed to the system control section 201. In the manner described above, the right angle sensor 132 and the right detection circuit 232 function as a detecting section that detects the right hip joint angle and the right hip joint angular speed of the user 900.

In the present embodiment, the system control section 201 determines the timing at which to generate the assist force by using, as a trigger, the left hip joint angle and the left hip joint angular speed obtained here. Since the left hip joint angle and the left hip joint angular speed are used as a trigger, appropriate step training can be provided to a rehabilitation patient with an injured right leg, without the limitation on the movement condition that the foot must contact the ground. Although explained in further detail below, there are cases where the left hip joint angle has extension set as the trigger angle direction and cases where the left hip joint angle has flexion set as the trigger angle direction. In a case where extension is set, the trigger is set to be ON, as the timing for generating the assist force, when the left hip joint angle is less than a threshold value. In a case where flexion is set, the trigger is set to be ON when the left hip joint angle is greater than a threshold value.

In general, when a step assist device is used for assisting with continuous stepping, the step assist device determines the timing at which to provide the assist force according to the step period. Step training is a type of training that involves a step movement of, while in a state where one leg is the pivot leg, moving the other leg forward and then returning the other leg to its original position. In other words, step training does not involve alternately moving the right and left legs, and therefore the period cannot be used when determining the timing at which to provide the assist force. In addition, there are cases where the timing at which the assist force is provided is determined such that the right and left step movements become symmetrical. As described above, step training does not involve alternately moving the left and right legs, and therefore it is impossible to consider left and right step movement symmetry. For these reasons, with a conventional step assist device, step training cannot be properly performed. Furthermore, with step training, there is a desire to correct the gait. With the present embodiment, as described in detail further below, upon deciding the timing at which to generate the assist force, the system control section 201 controls the left motor 121 and the right motor 122 according to an assistance plan set in advance for the step movement of a single step by the user 900.

The manipulating section 211 is a manipulation component for receiving instructions from the user 900, and includes the activation switch 101. In FIG. 2, the manipulating section 211 is represented by only the activation switch 101, but a manipulation component such as controls for receiving an assist force adjustment may be included. The system control section 201 performs control according to changes in the manipulation component detected by the manipulating section 211.

The memory 212 is a storage apparatus using a flash memory, such as an SSD, and stores the programs executed by the system control section 201, various parameter values, and the like in a manner to not be lost when the power supply is turned off. In the present embodiment, a torque table is stored in which counter values are associated with assist forces, as described further below. Furthermore, in the present embodiment, the memory 212 functions as a storage section that stores history information of the step movements of the user 900. The history information includes a signal waveform of the left hip joint angle, a signal waveform of the right hip joint angle, a signal waveform of the left hip joint angular speed, and a signal waveform of the right hip joint angular speed, which are all described further below. The history information further includes evaluation items for the progress of the step training Examples of the evaluation items for progress include the amplitude of the left hip joint angle and the right hip joint angle, the maximum values of the left hip joint angular speed and the right hip joint angular speed, the left hip joint angular speed and the right hip joint angular speed at a threshold angle, the maximum value and minimum value of the left hip joint angle, and the maximum value and minimum value of the right hip joint angle. The memory 212 functions as a work memory in which various values generated from the calculations performed by the system control section 201 are temporarily stored. The memory 212 may be formed from a plurality of types of memories that are physically isolated from each other, according to their respective uses.

The input/output interface 213 includes a communicating section that realizes input and output to and from an external device. For example, if the step assist device 100 is linked with a smartphone serving as the external device, the input/output interface 213 receives setting content that is set by the smartphone and transmits the history information stored in the memory 212 to the smartphone.

Figure 5:
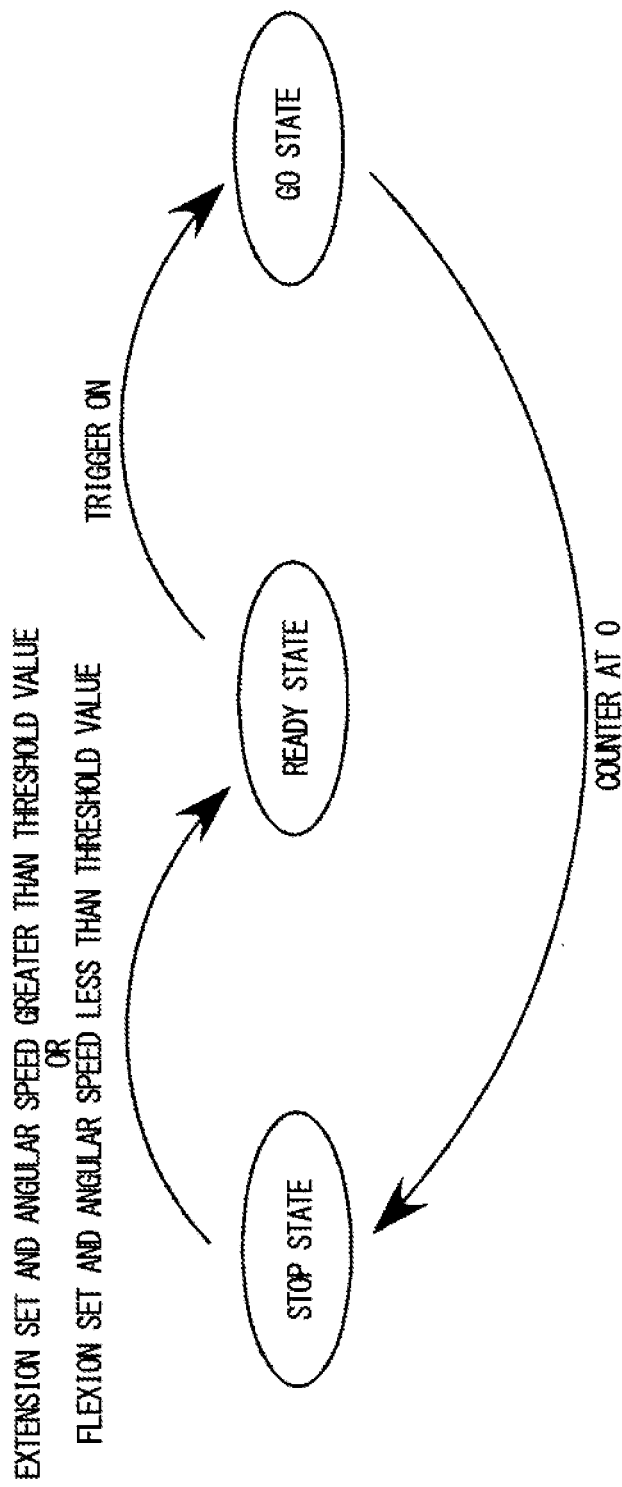
FIG. 5 shows a state transition of the operation of the step assist device.

FIG. 5 shows a state transition of the operation of the step assist device 100. The step assist device 100 assumes one operational state from among a STOP state, a READY state, and a GO state.

The STOP state is a state in which the supply of the assist force is stopped. When the power supply of the step assist device 100 is turned ON, the operational state is first set to the STOP state. After this, in a case where the direction of the left hip joint angle is set to extension as the trigger to be used, the step assist device 100 transitions to the READY state when the left hip joint angular speed becomes greater than a threshold value, and in a case where the direction of the left hip joint angle is set to flexion as the trigger to be used, the step assist device 100 transitions to the READY state when the left hip joint angular speed becomes less than a threshold value.

The READY state is a state of waiting to supply the assist force. Although described in detail further below, in the READY state, a threshold value calculation process and a trigger determination process are performed as the processes in the stage before transitioning to the GO state. After this, in a case where the trigger for providing the assist force is set to ON, the operational state transitions to the GO state.

The GO state is a state in which the supply of the assist force is performed. The assist force is supplied until a counter indicating the time for supplying the assist force reaches 0. When the counter reaches 0, the supply of the assist force is stopped, and the operational state transitions to the STOP state.

FIGS. 6A to 6E and FIGS. 7A to 7C are views for describing change in the waveform of each type of signal when step training is performed. The following describes an example of step training in which, in a state where the left leg of the user 900 is the pivot leg, the user 900 repeatedly performs an action that includes moving the right leg forward (swinging movement) and then returning the right leg to the original position (returning movement). Since each repeated movement is the same, this example focuses on a first instance of this movement. In this example, the counter value is set to 80, which is a value that corresponds to 0.8 seconds, the assist force is set to 4 N·m, and the trigger angle direction is set to extension. Furthermore, the threshold value for the right leg movement determination is set to 0, and the threshold value for the trigger determination is changed dynamically. The threshold value for the trigger determination is a threshold value that applies to the left hip joint angle. The threshold value for the trigger determination is described in detail further below.

Figure 6A:
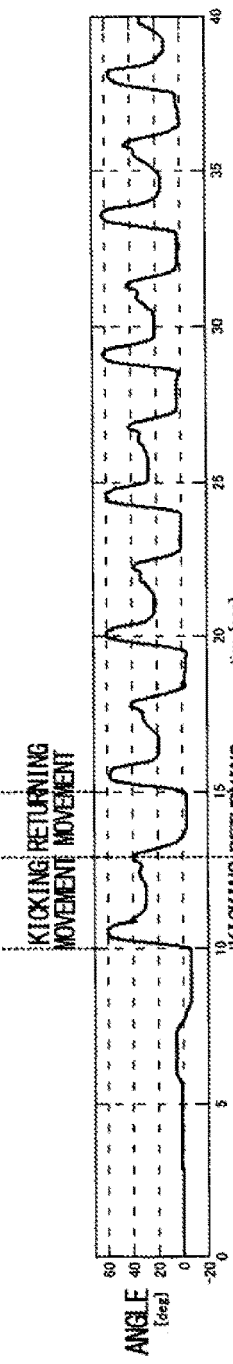
FIGS. 6A to 6E are views for describing change in the waveform of each type of signal when step training is performed.

FIG. 6A shows the signal waveform of the right hip joint angle, and shows the change over time of the right hip joint angle. The vertical axis indicates the right hip joint angle [deg] and the horizontal axis indicates time [sec].

Figure 6B:
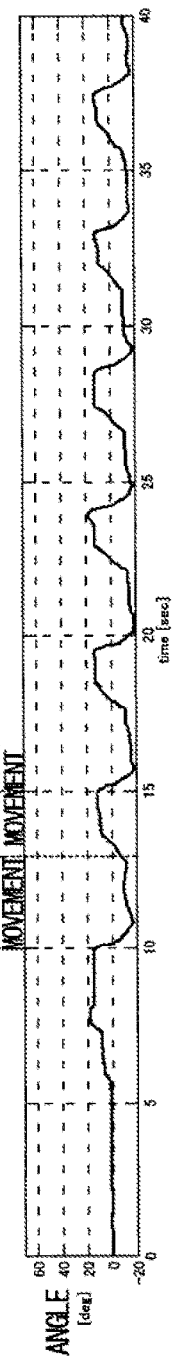

FIG. 6B shows the signal waveform of the left hip joint angle, and shows the change over time of the left hip joint angle. The vertical axis indicates the left hip joint angle [deg] and the horizontal axis indicates time [sec].

Figure 6C:
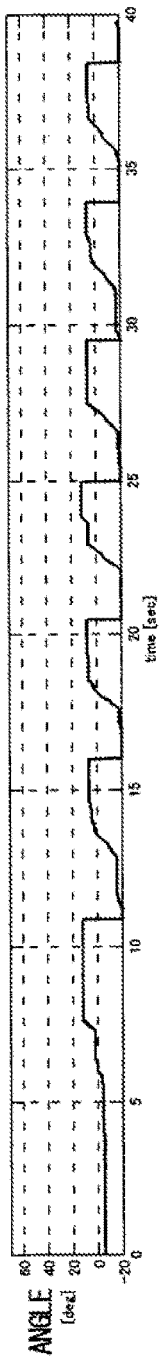

FIG. 6C shows the changes of the threshold value for the trigger determination, which applies to the left hip joint angle. The vertical axis indicates the angle [deg] and the horizontal axis indicates time [sec].

Figure 6D:
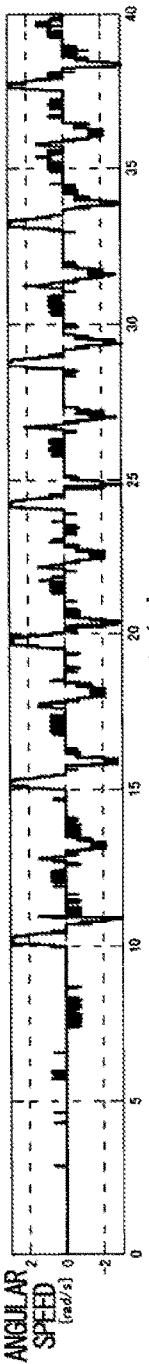

FIG. 6D shows the signal waveform of the right hip joint angular speed, and shows the change over time of the right hip joint angular speed. The vertical axis indicates the right hip joint angular speed [rad/s] and the horizontal axis indicates time [sec].

Figure 6E:
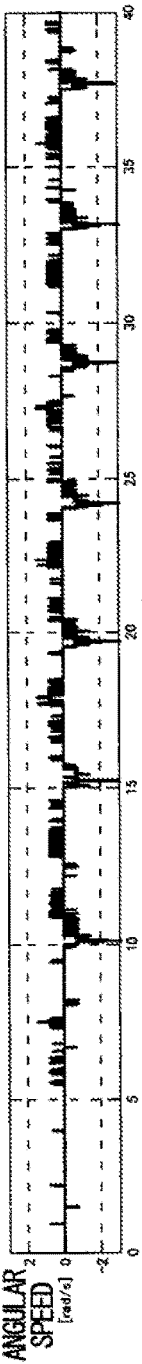

FIG. 6E shows the signal waveform of the left hip joint angular speed, and shows the change over time of the left hip joint angular speed. The vertical axis indicates the left hip joint angular speed [rad/s] and the horizontal axis indicates time [sec].

Figure 7A:
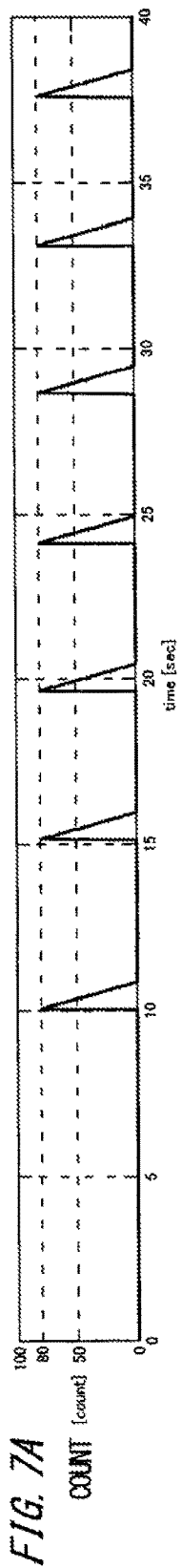
FIGS. 7A to 7C are views for describing change in the waveform of each type of signal when step training is performed.

FIG. 7A shows the changes of the counter value. The vertical axis indicates the counter value [count] and the horizontal axis indicates time [sec].

Figure 7B:
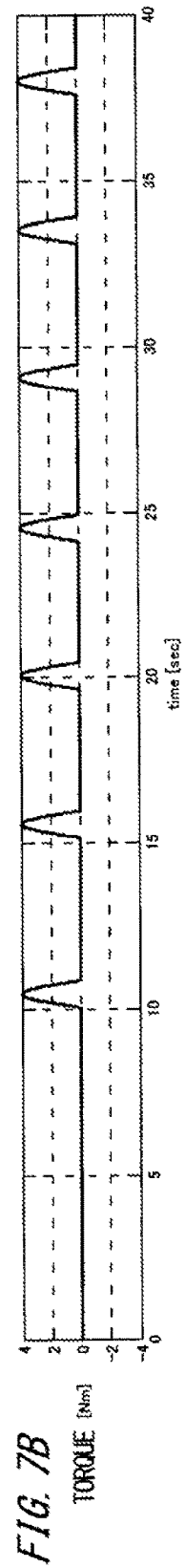

FIG. 7B shows the changes of the torque generated by the right motor 122. The vertical axis indicates the torque [N·m] and the horizontal axis indicates time [sec].

Figure 7C:
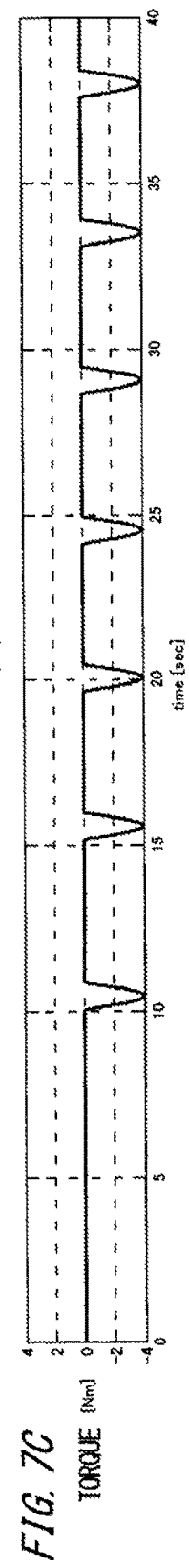

FIG. 7C shows the changes of the torque generated by the left motor 121. The vertical axis indicates the torque [N·m] and the horizontal axis indicates time [sec].

As described above, the operational state is first set to the STOP state. As shown in FIG. 6E, at around 1 second, a positive value is detected for the left hip joint angular speed. Accordingly, at this time, the operational state transitions to the READY state. After this, as shown in FIG. 6A, at around 10 seconds, the right hip joint angle suddenly increases monotonically. This indicates that the right leg is swinging. As a result of the forward movement of the right leg, the center line of the upper body 910 in the direction of gravity shown in FIG. 3 moves forward, and therefore, as shown in FIG. 6B, the left hip joint angle relatively decreases. When this happens, as shown in FIGS. 6B and 6C, the left hip joint angle drops below the threshold value for the trigger determination.

When the left hip joint angle drops below the threshold value, the operational state transitions to the GO state. As shown in FIG. 7A, the system control section 201 sets a value for the counter. As shown in FIGS. 7B and 7C, the assist force is supplied to the thigh of the left leg and the thigh of the right leg until the counter value reaches 0. Specifically, the system control section 201 controls the left motor 121 to generate an assist force that presses down and backward on the thigh of the left leg and controls the right motor 122 to generate an assist force that presses upward and forward on the thigh of the right leg. Accordingly, the assist force acting on the thigh of the left leg has a negative value and the assist force acting on the thigh of the right leg has a positive value. As shown in FIG. 7B, the assist force generated by the right motor 122 acts like a half period of a sine curve that gradually becomes more positive up to the center of the count period and then gradually becomes less positive. On the other hand, as shown in FIG. 7C, the assist force generated by the left motor 121 gradually becomes more negative up to the center of the count period and then gradually becomes less negative.

In the manner described above, the step assist device 100 can provide the assist force for one step to the thigh of the left leg and the thigh of the right leg. By providing the assist force to the thigh of the left leg, the left hip joint angle becomes smaller by approximately −20 [deg]. Since the kicking is assisted by the assist force acting backward on the left thigh, the gait is corrected. Furthermore, by providing the assist force to the thigh of the right leg, in the present embodiment, the right hip joint angle is increased by approximately 60 [deg]. Since the swinging assistance causes an increase in the knee bending angle, the gait of the user 900 is corrected. After this, after the right hip joint angle has moved by about 30 [deg], the right hip joint angle decreases monotonically and, at around 13 seconds, reaches approximately 0 [deg]. In other words, the right leg that had been moved forward returns to the original position. After this, at around 15 seconds, the right hip joint angle again suddenly increases monotonically. In other words, the second movement begins.

The swinging movement of an injured right leg might be more unnatural than the swinging movement of a healthy right leg. Accordingly, when setting the trigger angle for the swinging movement of the injured right leg, there might be instances where it is impossible to begin the assistance operation at the correct timing. Therefore, if the left leg, which is the opposite of the right leg undergoing the rehabilitation, is healthy, then the trigger angle may be set for the kicking movement of the left leg. If the movement of the healthy left leg is the detection target, then the assistance operation can be started stably. It was confirmed through experimentation that the effect of step training is maximized by setting the healthy left leg as the leg that is the target of the trigger determination.

In step training, it is possible to conceive of a method that uses the knee angle of the user 900 as the trigger for determining the timing at which to generate the assist force. However, when the user 900 moves their right leg forward, the knee angle of the left leg, which is the pivot leg, changes by a small amount. In other words, during step training, there is no correlation between the change in the knee angle of the left leg and the swinging movement of the right leg. Therefore, it is difficult to appropriately determine the timing at which to generate the assist force for the right leg based on the knee angle of the left leg. On the other hand, as described in FIGS. 6A to 6E, the right hip joint angle increases monotonically as a result of the right leg moving forward, while the left hip joint angle relatively decreases. In other words, during the step training, there is a correlation between the change in the left hip joint angle and the swinging movement of the right leg. Therefore, in the present embodiment, the hip joint angles are used as the triggers for determining the timing at which to generate the assist force. Since there is a correlation between the change in the left hip joint angle and the swinging movement of the right leg, the right leg can be supplied with the assist force by using the left hip joint angle as a trigger. In other words, the leg serving as the target for the trigger angle and the leg serving as the target for the supply of assist force can be different.

Figure 8:
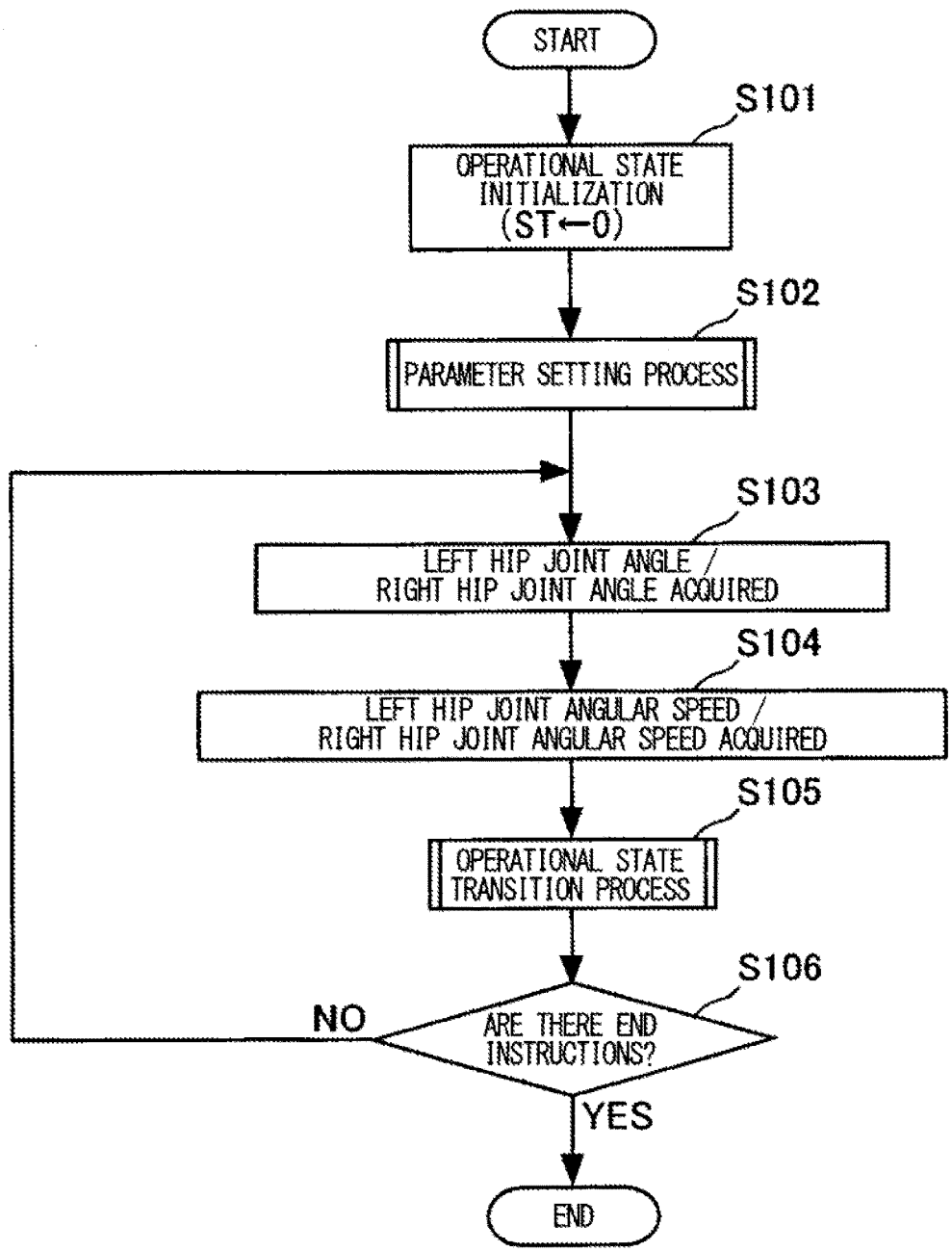
FIG. 8 is a flow chart showing the overall flow of the step assist process.

FIG. 8 is a flow chart showing the overall flow of the step assist process. In this flow, ST is a variable indicating the operational state of the step assist device 100. Here, 0 indicates the STOP state, 1 indicates the READY state, and 2 indicates the GO state. This flow is started when the power supply of the step assist device 100 is turned on.

The system control section 201 initializes the operational state of the step assist device 100 (step S101). Specifically, the system control section 201 substitutes 0 for ST.

The system control section 201 performs the parameter setting process (step S102). The details of the parameter setting process are described further below.

The system control section 201 acquires the left hip joint angle and the right hip joint angle (step S103). The system control section 201 acquires the left hip joint angle and the right hip joint angle periodically. For example, these angles may be acquired every 10 ms.

The system control section 201 acquires the left hip joint angular speed and the right hip joint angular speed (step S104). The system control section 201 acquires the left hip joint angular speed and the right hip joint angular speed periodically. For example, these angular speeds may be acquired every 10 ms.

The system control section 201 performs the state transition process (step S105). The details of the state transition process are described further below.

The system control section 201 determines whether end instructions have been received (step S106). If end instructions have not been received, the process moves to step S103. If end instructions have been received (YES at step S106), the process is ended and the power supply from the battery 102 is stopped.

Figure 9:
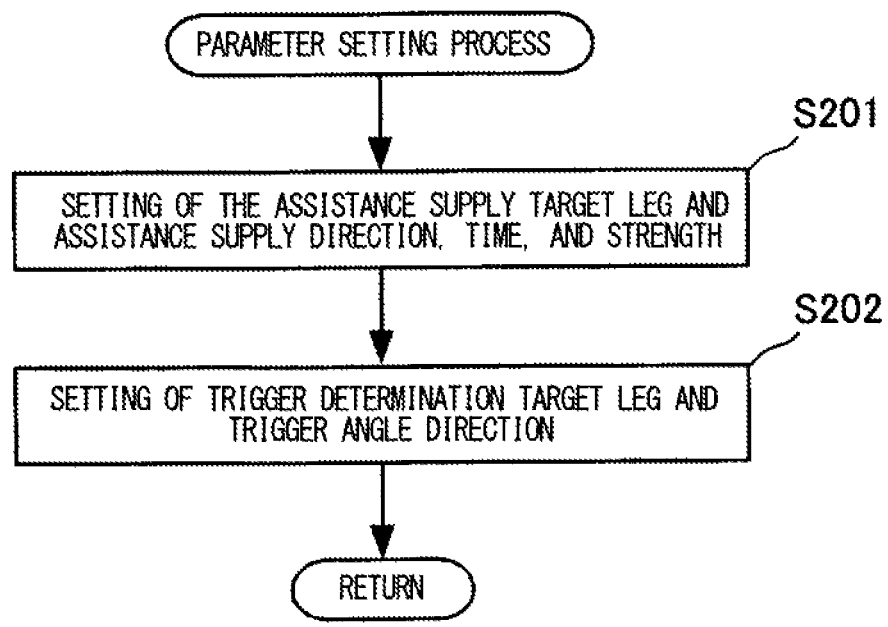
FIG. 9 is a sub-flow chart showing the flow of the parameter setting process.

FIG. 9 is a sub-flow chart showing the flow of the parameter setting process. By performing the parameter setting process, the system control section 201 presets the assistance plan for one step, prior to providing the assist force. The assistance plan for one step includes the direction, time, and strength of the provided assist force, as described further below.

The system control section 201 sets the leg that is to be the target of the supplied assist force, and also the direction, time, and strength of the supplied assist force (step S201). Using the example of the step training described using FIGS. 6A to 6E and 7A to 7C, the right leg and the left leg are set as legs that are the targets for the supplied assist force. The direction of the supplied assist force is set to be the flexion direction for the right leg and the extension direction for the left leg. The time for which the assist force is supplied is set to 0.8 seconds, and the strength is set to 4 N·m.

The system control section 201 sets the foot that is to be the target for the trigger determination and the direction of the trigger angle (step S202). Using the example of the step training described using FIGS. 6A to 6E and 7A to 7C, the right leg is set to be the target of the trigger determination and the extension direction is set as the trigger angle direction. When the above settings are completed, the process returns to the main flow.

Figure 10:
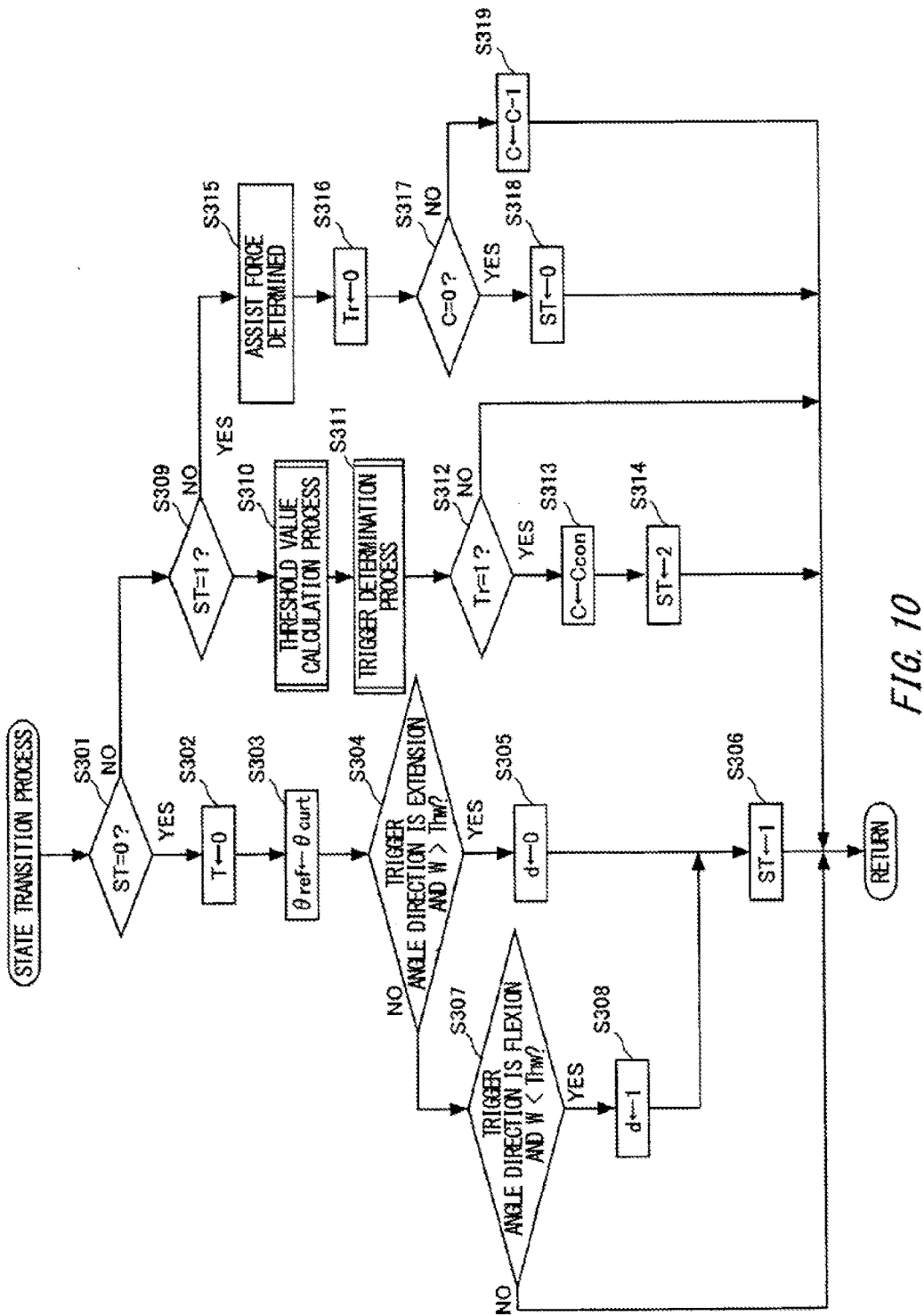
FIG. 10 is a sub-flow chart showing the flow of the state transition process.

FIG. 10 is a sub-flow chart showing the flow of the state transition process. In this flow, as explained above, ST is a variable indicating the operational state of the step assist device 100. Furthermore, T is a variable indicating the assist force. Also, d is a variable indicating the direction of the trigger angle for the provided assist force, where 0 indicates extension and 1 indicates flexion. Yet further, Tr is a variable indicating ON/OFF of the trigger, where 0 indicates OFF and 1 indicates ON. In addition, θref indicates a reference angle that is a reference hip joint angle for the leg that is the trigger determination target, θcurt indicates a current angle that is the current hip joint angle of the leg that is the trigger determination target, W indicates the hip joint angular speed of the leg that is the trigger determination target, Thw indicates the threshold value of the hip joint angular speed, C indicates the current counter value, and Ccon indicates a preset counter value.

The system control section 201 determines whether ST=0 (step S301). If ST=0, i.e. if the operational state is the STOP state (YES at step S301), the assist force is not supplied, and therefore 0 is substituted for T (step S302). Then, in order to initialize the reference angle θref, the current angle θcurt is substituted for the reference angle θref (step S303).

The system control section 201 determines whether the trigger angle direction is extension and whether W>Thw (step S304). Using the example of the step training described using FIGS. 6A to 6E and 7A to 7C, the trigger determination target leg is the left leg and the trigger angle direction is extension, and therefore, if the left hip joint angular speed W is greater than the threshold value Thw (YES at step S304), the process moves to the following step S305. Since the trigger angle direction is extension, 0 is substituted for d (step S305), and 1 is substituted for ST (step S306) in order to transition the operational state to the READY state.

As described above, in the present embodiment, when the trigger angle direction is extension, the operational state is transitioned to the READY state when W>Thw, and is not immediately transitioned to the READY state. Using the example of the step training described using FIGS. 6A to 6E and 7A to 7C, in a case where the trigger angle direction is extension, the time when W>Thw is the time when the left leg is moving forward. As an example, with a condition that the left leg is moving in the extension direction, after the assist force is supplied once, the assist force is incorrectly applied again if the left leg of the user 900 moves farther in the extension direction. In other words, there is a problem that the assist force is supplied a plurality of times for a single step. By using the condition that W>Thw, the assist force is not supplied unless the left foot is moved forward once, and therefore it is possible to avoid supplying the assist force a plurality of times for a single step.

If the trigger angle direction is not extension, i.e. if the trigger angle direction is flexion, or if W≤Thw (NO at step S304), the system control section 201 determines whether the trigger angle direction is flexion and whether W<Thw (step S307). If the trigger angle direction is flexion and W<Thw (YES at step S307), the trigger angle direction is flexion, and therefore 1 is substituted for d (step S308) and 1 is substituted for ST (step S306).

If it is not the case that ST=0, i.e. if the operational state is not the STOP state (NO at step S301), the system control section 201 determines whether ST=1 (step S309). If ST=1, i.e. if the operational state is the READY state (YES at step S309), the system control section 201 performs the threshold value calculating process and the trigger determination process (steps S310 and S311). Although explained in detail further below, the threshold value is calculated in real time and the calculated threshold value is used in the trigger determination. Using the example of the step training described using FIGS. 6A to 6E and 7A to 7C, the operational state transitions to the READY state when the left leg moves forward.

The system control section 201 determines whether Tr=1 (step S312). If Tr=1 (YES at step S312), then Ccon is substituted for C (step S313). Using the example of the step training described using FIGS. 6A to 6E and 7A to 7C, a counter value corresponding to 0.8 ms is substituted in.

Then, in order to transition the operational state to the GO state, 2 is substituted for ST (step S314).

If it is not the case that ST=1, i.e. if the operational state is not the READY state (NO at step S309), this means that the operational state is the GO state. In this case, the system control section 201 supplies the assist force until the preset counter value reaches 0. Specifically, the system control section 201 references the torque table and determines the assist force corresponding to the current counter value (step S315), and substitutes 0 or Tr (step S316). The system control section 201 then determines whether C=0 (step S317). If C=0 (YES at step S317), 0 is substituted for ST (step S318) in order to transition the operational state to the STOP state. If it is not the case that C=0 (NO at step S317), C−1 is substituted for C (step S319).

The process returns to the main flow after any one of steps S306, S314, S318, or S319, if a "NO" determination is made at step S307, or if a "NO" determination is made at step S312.

Figure 11:
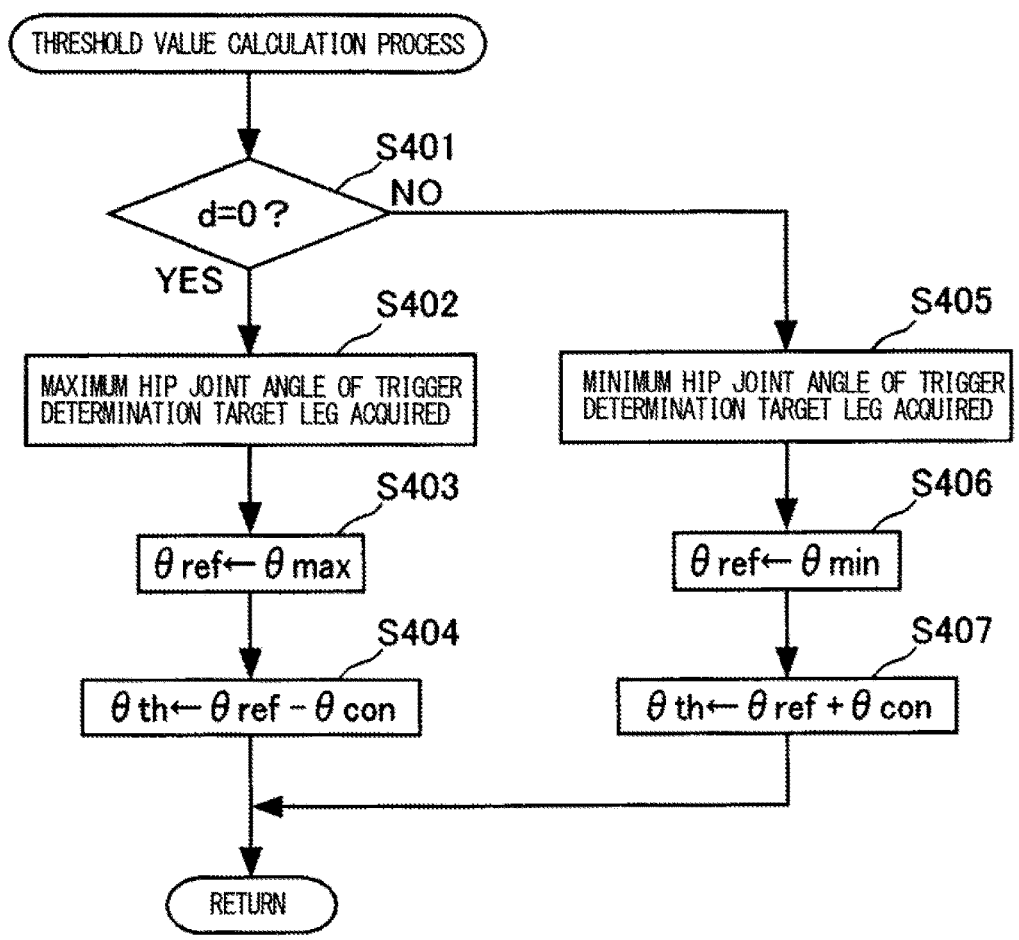
FIG. 11 is a sub-flow chart showing the flow of the threshold value calculation process.

FIG. 11 is a sub-flow chart showing the flow of the threshold value calculation process. In this flow, as described above, d is a variable indicating the direction of the trigger angle for the supply of the assist force, and θref indicates a reference angle that is a reference hip joint angle for the leg that is the trigger determination target. Furthermore, θmax indicates the maximum hip joint angle for the trigger determination target leg and θmin indicates the minimum hip joint angle for the trigger determination target leg. Yet further, θth indicates the threshold value for the hip joint angle, and θcon indicates a preset constant.

The system control section 201 determines whether d=0 (step S401). If d=0, i.e. if the trigger angle direction is extension (YES at step S401), the system control section 201 acquires the maximum hip joint angle θmax for the trigger determination target leg (step S402). Using the example of the step training described using FIGS. 6A to 6E and 7A to 7C, the system control section 201 acquires the maximum value of the left hip joint angle. The system control section 201 substitutes θmax for θref (step S403) and substitutes θref−θcon for θth (step S404).

Here, the user might be a person who can spread their legs fairly widely or might be a person who cannot spread their legs widely. Accordingly, if the threshold value θth is a fixed value, there are cases where it is difficult for the user to move far enough to exceed the threshold value θth.

In the present embodiment, the threshold value θth is variable and is calculated dynamically. When the trigger angle direction is extension, the threshold value θth is calculated using the maximum hip joint angle θmax of the user. Accordingly, the threshold value θth can be set to a value corresponding to the user. In this way, it is possible to restrict problems, such as the assist force not being provided, caused by variation in the movements of the user.

If it is not the case that d=0, i.e. if the trigger angle direction is flexion (NO at step S401), the system control section 201 acquires the minimum hip joint angle θmin of the trigger determination target leg (step S405). Using the example of the step training described using FIGS. 6A to 6E and 7A to 7C, the system control section 201 acquires the minimum value of the left hip joint angle. The system control section 201 substitutes θmin for θref (step S406) and substitutes θref+θcon for θth (step S407).

As described above, in the present embodiment, the threshold value θth is variable and is calculated dynamically. When the trigger determination direction is flexion, the threshold value θth is calculated using the minimum hip joint angle θmin of the user. Accordingly, the threshold value θth can be set to a value corresponding to the user. In this way, it is possible to restrict problems, such as the assist force not being provided, caused by variation in the movements of the user.

When the threshold value θth has been calculated at step S404 or step S407, the process returns to the main flow.

As described above, the system control section 201 uses the threshold value for flexion when there is flexion movement and uses the threshold value for extension when there is extension movement. The system control section 201 calculates the threshold value for extension using the extension angle of the user, and calculates the threshold value for flexion using the flexion angle of the user. By using threshold values that are suitable for the respective movements, it is possible to appropriately perform the trigger determination process described further below.

Figure 12:
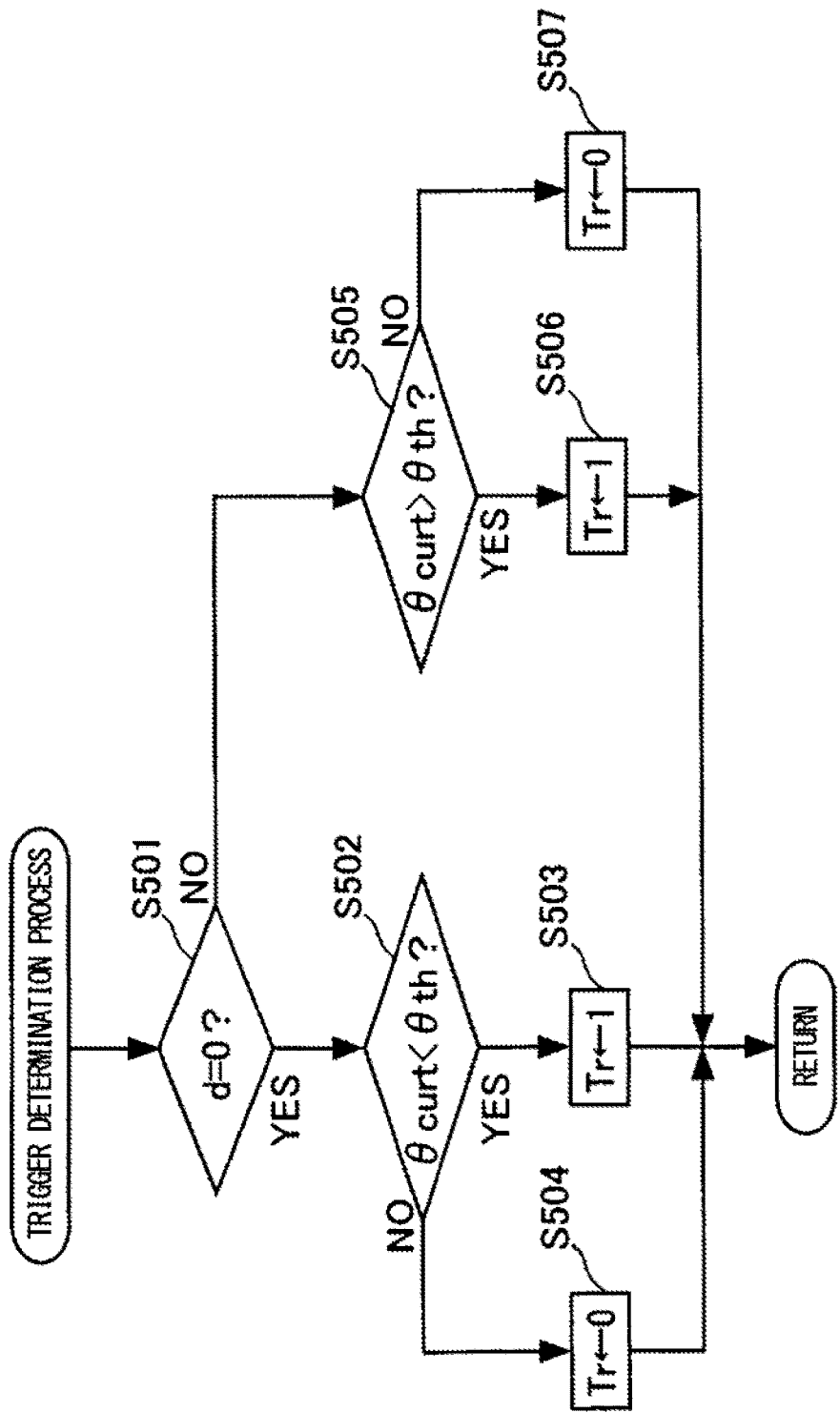
FIG. 12 shows a sub-flow chart showing the flow of the trigger determination process.

FIG. 12 shows a sub-flow chart showing the flow of the trigger determination process. In this flow, as described above, d is a variable indicating the trigger angle direction for the supply of assist force and Tr is a variable indicating ON/OFF for the trigger. Furthermore, θth indicates the threshold value for the hip joint angle, and θcurt indicates the current angle, which is the current hip joint angle of the trigger determination target foot.

The system control section 201 determines whether d=0 (step S501). If d=0, i.e. if the trigger angle direction is extension (YES at step S501), the system control section 201 determines whether θcurt<θth (step S502). If θcurt<θth (YES at step S502), the system control section 201 substitutes 1 for Tr (step S503) in order to turn ON the trigger. If θcurt≥θth (NO at step S502), the system control section 201 substitutes 0 for Tr (step S504) in order to turn OFF the trigger.

If it is not the case that d=0, i.e. if the trigger angle direction is flexion (NO at step S501), the system control section 201 determines whether θcurt>θth (step S505). If θcurt>θth (YES at step S505), the system control section 201 substitutes 1 for the Tr (step S506) in order to turn ON the trigger. If θcurt≤θth (NO at step S505), the system control section 201 substitutes 0 for Tr in order to turn OFF the trigger (step S507).

After a value is substituted for Tr in any one of steps S503, S504, S506, or S507, the process returns to the main flow.

The system control section 201 may change the assistance plan according to the progress made in the step training. In this case, the system control section 201 may compare each evaluation item in the progress to respective evaluation references set in advance, and adjust at least one of the time for which the assist force is supplied and the strength of the assist force, according to the comparison results. For example, in a case where each of the evaluation items exhibits a value higher than the corresponding evaluation reference, the system control section 201 shortens the time for which the assist force is supplied and reduces the strength of the assist force. Gradually weakening the assist force according to the progress in this manner can be expected to urge the user 900 to walk with their own strength. On the other hand, if there are evaluation items that fall below the evaluation references, the time for which the assist force is supplied is increased and the strength of the assist force is also increased. In this way, it is expected suitable assistance can be provided to the user 900. In the manner described above, by using all of the evaluation items for progress, the accuracy of the evaluation of progress can be increased.

On the other hand, the system control section 201 may adjust the time for which the assist force is supplied and the strength of the assist force by using a portion of evaluation items from among the plurality of evaluation item examples. For example, the amplitude of the left hip joint angle and the right hip joint angle, which is an item that is strongly indicative of progress, may be used. Furthermore, which evaluation items are used may be determined by a selection from the user 900. As described above, in a case where all of the evaluation items for progress are used, the accuracy of the progress evaluation can be increased, and therefore when using all of the evaluation items for progress, the system control section 201 may set the step period for determining each evaluation item to be shorter than when using a portion of the evaluation items.

The system control section 201 may change the number of evaluation items used, according to the state of the progress during the step training. For example, in the initial stage of the step training, the system control section 201 uses a portion of the evaluation items from among the plurality of evaluation item examples. In this case, the user 900 can proceed slowly with the step training in a manner to first fulfill the evaluation references for this portion of the evaluation items. On the other hand, in the final stage of the step training, the system control section 201 uses all of the evaluation item examples. In this case, the user 900 can perform the step training with a feeling of accomplishment by fulfilling all the evaluation references for all of the evaluation items.

In the above description, the system control section 201 supplies the assist force only for a predetermined time, but the assist force may be supplied until at least one of the left hip joint angle $\theta_L$ and the right hip joint angle $\theta_R$ reaches a predetermined hip joint angle. In the above description, the threshold value θth is variable, but may instead be fixed. In this case, as described above, the threshold value is preferably set to be relatively small, in order to avoid problems such as the assist force not being supplied due to variations in the movement of the user. In the above description, θcon is a predetermined constant, but may instead be variable according to the amplitude of the angle or the reference angle.

In the above description, the system control section 201 determines the timing at which the assist force is generated by using either the left hip joint angle $\theta_L$ or the right hip joint angle $\theta_R$, but may instead determine the timing at which the assist force is generated by using both the left hip joint angle $\theta_L$ and the right hip joint angle $\theta_R$. For example, the system control section 201 may generate the assist force when the left hip joint angle $\theta_L$ is below a threshold value for left extension assistance and the right hip joint angle $\theta_R$ is above a threshold value for right flexion assistance.

In the above description, the system control section 201 supplies the assist force to both legs, but may instead supply the assist force to only one of the legs. In this case, the leg that is the target for supplying the assist force may be different from the trigger determination target leg. Specifically, the system control section 201 may drive the right motor 122 according to the assistance plan when the left hip joint angle $\theta_L$ exceeds the threshold value θth, and may drive the left motor 121 according to the assistance plan when the right hip joint angle $\theta_R$ exceeds the threshold value θth. With this configuration, the healthy leg can be set as the trigger determination leg and the injured leg can be set as the leg that is the target of the assist force supply, thereby decreasing the burden on the user.

In the above description, the assist force is supplied to the right and left legs in response to the swinging movement of the right leg, but instead the assist force may be supplied to the right and left legs in response to the returning movement of the right leg. In this case, the left leg may be set as the trigger determination target leg and the flexion direction may be set as the trigger angle direction.

In the above description, a case of rehabilitation of the right leg using the step assist device 100 is provided as an example, but obviously the step assist device 100 can also be used for rehabilitation of the left leg. In this case, the step assist device 100 may determine the timing at which to generate the assist force by using the right hip joint angle and the right hip joint angular speed. Specifically, the step assist device 100 determines the timing at which to generate the assist force to be the timing at which a positive value is detected for the right hip joint angular speed and the right hip joint angle is less than the trigger determination threshold value. The step assist device 100 may drive the right motor 122 according to the assistance plan in order to supply the right leg with the assist force for assisting with the extension movement, and may drive the left motor 121 according to the assistance plan in order to supply the left leg with the assist force for assisting with the flexion movement. The threshold value used for the left hip joint angle and the threshold value used for the right hip joint angle may be different from each other. Furthermore, the assistance plan used when a positive value is detected for the right hip joint angular speed and the right hip joint angle is less than the trigger determination threshold value may be different from the assistance plan used when a positive value is detected for the left hip joint angular speed and the left hip joint angle is less than the trigger determination threshold value. The above description provides an example in which one leg of the user 900 is injured, but in a case where both legs of the user 900 are injured, the trigger determination target leg may be set as desired according to the state of each leg. For example, the leg that experiences a lesser degree of paralysis may be set as the trigger determination target.

In the above description, the system control section 201 causes the left motor 121 and the right motor 122 to supply the same assist force at the same time, but may instead cause the left motor 121 and the right motor 122 to supply different assist forces or to supply the assist force at different times. By suitably adjusting the assist forces and the assistance time for the left leg and the right leg depending on the user 900, the gait can be corrected more appropriately.

In the above description, the step assist device 100 is used for step training, but may instead be used for static walking, which is walking in place. In this case, the control described for rehabilitating the right leg and the control described for rehabilitating the left leg may be combined. Furthermore, the step assist device 100 may be used for training in which the step width does not span a single step. In this case, the step assist device 100 supplies the assist force according to an assistance plan for less than one step that is set in advance.

In the above description, the history information includes the signal waveform of the left hip joint angle, the signal waveform of the right hip joint angle, the signal waveform of the left hip joint angular speed, and the signal waveform of the right hip joint angular speed, but when considering the calculation of the trigger determination threshold value used for the left hip joint angle, only the signal waveform of the left hip joint angle need be included.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

LIST OF REFERENCE NUMERALS

100: step assist device, 101: activation switch, 102: battery, 103: waist frame, 104: waist belt, 121: left motor, 122: right motor, 131: left angle sensor, 132: right angle sensor, 141: left thigh frame, 142: right thigh frame, 151: left thigh belt, 152: right thigh belt, 201: system control section, 211: manipulating section, 212: memory, 213: input/output interface, 221: left control circuit, 222: right control circuit, 231: left detection circuit, 232: right detection circuit, 900: user, 901: left thigh, 902: right thigh, 910: upper body

What is claimed is:

1. A step assist device comprising:
   a providing section configured to provide an assist force to one of a leg in the midst of flexion movement and a leg in the midst of extension movement;
   a detecting section that detects a hip joint angle, which is an angle of aperture of a hip joint of a user; and
   a processor configured to:
      begin control causing the providing section to provide the assist force to the leg in the midst of flexion movement, in response to the detecting section detecting that the hip joint angle of the leg in the midst of extension movement has exceeded a first predetermined threshold value, and continue causing the providing section to provide the assist force until the hip joint angle of the leg in the midst of extension movement reaches a first predetermined angle, the first predetermined angle being greater than the first predetermined threshold value, according to an assistance plan that is set in advance for a step movement of a single step of the user, and
      begin control causing the providing section to provide the assist force to the leg in the midst of extension movement, in response to the detecting section detecting that the hip joint angle of the leg in the midst of flexion movement has exceeded a second predetermined threshold value, and continue causing the providing section to provide the assist force until the hip joint angle of the leg in the midst of flexion movement reaches a second predetermined angle, the second predetermined angle being greater than the second predetermined threshold value, according to the assistance plan that is set in advance for the step movement of a single step of the user.

2. The step assist device according to claim 1, comprising:
   a storage section that stores, as history information, at least change over time of the hip joint angle during the step movement, wherein
   the processor is further configured to change the first and second predetermined threshold values based on the history information.

3. The step assist device according to claim 2, wherein the processor is further configured to change the assistance plan based on the history information.

4. The step assist device according to claim 3, wherein the processor is further configured to change, as the assistance plan, at least one of time during which the assist force is provided and strength of the assist force.

5. The step assist device according to claim 1, wherein the processor is further configured to control the providing section, according to the assistance plan, to provide the assist force only for a predetermined time or to provide the assist force until the hip joint angle reaches the first or second predetermined angle.

6. The step assist device according to claim 1, wherein the processor is further configured to use the second predetermined threshold value for flexion movement when the leg in the midst of flexion movement is raising a thigh toward a stomach region, and use the first predetermined threshold value for extension movement when the leg in the midst of extension movement is lowering a raised thigh.

7. The step assist device according to claim 6, wherein the processor is further configured to calculate the first predetermined threshold value based on an extension angle of the leg in the midst of extension movement, and calculate the second predetermined threshold value based on a flexion angle of the leg in the midst of flexion movement.

8. The step assist device according to claim 1, wherein the detecting section also detects hip joint angular speed of the user, and
the processor is further configured to begin controlling the providing section when a condition set in advance for the hip joint angular speed is also satisfied.

9. The step assist device according to claim 1, wherein the providing section includes a left actuator that provides the assist force to a left leg of the user and a right actuator that provides the assist force to a right leg of the user,
the detecting section includes a left angle sensor that detects left hip joint angle of the user and a right angle sensor that detects right hip joint angle of the user, and
the processor is further configured to drive at least one of the left actuator and the right actuator according to the assistance plan, when at least one of the left hip joint angle and the right hip joint angle exceeds the first or second predetermined threshold value.

10. The step assist device according to claim 9, wherein the processor is further configured to perform at least one of first drive control that includes driving the right actuator according to the assistance plan when the left hip joint angle exceeds the first or second predetermined threshold value and second drive control that includes driving the left actuator according to the assistance plan when the right hip joint angle exceeds the first or second predetermined threshold value.

11. The step assist device according to claim 10, wherein the processor is further configured to perform the first drive control when the left leg performs the extension movement during the step movement of the user and perform the second drive control when the right leg performs the extension movement during the step movement of the user.

12. The step assist device according to claim 11, wherein the processor is further configured to drive the right actuator and also drive the left actuator according to the assistance plan, as the first drive control, and drive the left actuator and also drive the right actuator according to the assistance plan, as the second drive control.

13. The step assist device according to claim 10, wherein the first or second predetermined threshold value used for the left hip joint angle and the first or second predetermined threshold value used for the right hip joint angle are different from each other.

14. The step assist device according to claim 10, wherein the assistance plan used for the first drive control and the assistance plan used for the second drive control are different from each other.

15. The step assist device according to claim 1, wherein the providing section is configured to press upward and forward on a thigh of the leg in the midst of flexion movement while pressing down and backward on a thigh of the leg in the midst of extension movement.

16. A computer-readable medium storing thereon a step assistance program that, when executed by a computer, causes the computer to:
detect a hip joint angle, which is an angle of aperture of a hip joint of a user;
begin control causing a providing section configured to provide an assist force to one of a leg in the midst of flexion movement and a leg in the midst of extension movement to provide the assist force to the leg in the midst of flexion movement, in response to detecting that the hip joint angle of the leg in the midst of extension movement has exceeded a first predetermined threshold value, and continue causing the providing section to provide the assist force until the hip joint angle of the leg in the midst of extension movement reaches a first predetermined angle, the first predetermined angle being greater than the first predetermined threshold value, according to an assistance plan that is set in advance for a step movement of a single step of the user; and
begin control causing the providing section to provide the assist force to the leg in the midst of extension movement, in response to detecting that the hip joint angle of the leg in the midst of flexion movement has exceeded a second predetermined threshold value, and continue causing the providing section to provide the assist force until the hip joint angle of the leg in the midst of flexion movement reaches a second predetermined angle, the second predetermined angle being greater than the second predetermined threshold value, according to the assistance plan that is set in advance for the step movement of a single step of the user.

* * * * *